United States Patent [19]
Aoyama et al.

[11] Patent Number: 5,945,562
[45] Date of Patent: Aug. 31, 1999

[54] PROCESS OF PREPARING PERFLUOROALKYLCARBOXYLIC ACID

[75] Inventors: Hirokazu Aoyama; Yasumichi Chiba, both of Osaka, Japan

[73] Assignee: Daikin Industries Ltd., Osaka, Japan

[21] Appl. No.: 09/014,179

[22] Filed: Jan. 27, 1998

[30] Foreign Application Priority Data

Feb. 7, 1997 [JP] Japan .................................. 9-024874
Nov. 27, 1997 [JP] Japan .................................. 9-325897

[51] Int. Cl.$^6$ .................................................. C07C 51/16
[52] U.S. Cl. ......................................................... 562/544
[58] Field of Search ............................................. 562/544

[56] References Cited

U.S. PATENT DOCUMENTS 4,751,027  6/1988  Von Werner et al. ................... 260/408
5,820,665  10/1998  Kai ..................................... 106/287.28

FOREIGN PATENT DOCUMENTS 44-7691   4/1969  Japan .
50-157314 12/1975  Japan .

OTHER PUBLICATIONS

Journal of Flourine Chemistry, "Oxidative Cleavage of Partially or Perfluorinated Olefins by Ruthenium Tetroxide", 13 (1979) 175–177.

Primary Examiner—Samuel Barts
Assistant Examiner—Rosalynd Keys
Attorney, Agent, or Firm—Birch, Stewart, Kolasch & Birch, LLP

[57] ABSTRACT

A process of preparing a perfluoroalkylcarboxylic acid by an oxidative decomposition reaction of a perfluoroalkylethylene corresponding to a general formula:

$$Rf-CH=CH_2$$

[wherein, Rf is a perfluoroalkyl group containing 2 to 14 carbon atoms.]

to obtain a perfluoroalkylcarboxylic acid corresponding to a general formula:

$$Rf-COOH$$

[wherein, Rf is the same as the above.]

characterized that the reaction is carried out in the presence of an organic solvent which is compatible with water and substantially inert to the above reaction, a ruthenium compound as a catalyst and an aqueous solution of at least one of hypochlorous acid or a salt thereof is provided.

20 Claims, No Drawings

PROCESS OF PREPARING PERFLUOROALKYLCARBOXYLIC ACID

BACKGROUND OF THE INVENTION

1. Field of the Invention

The present invention relates to a process of preparing at least one of perfluoroalkylcarboxylic acids, for example, perfluorooctylcarboxylic acid.

2. Description of the Related Art

Perfluoroalkylcarboxylic acids are industrially useful compounds as feedstocks for surface-active agents, water- and oil-repellant agents, and medicines and agricultural chemicals. Conventional processes of preparing these compounds are generally as follows:

(1) Electrolytic fluorination process using a hydrocarbon compound as a feedstock,
(2) Production process by the reaction of fuming sulfuric acid and perfluoroalkyliodide,
(3) Production process by the reaction of perfluoroalkyliodide and carbon dioxide,
(4) Oxidative decomposition process using an oxidant such as a dichromate or a permanganate in which a perfluoroalkylolefin is used as a feedstock (see for example, Japanese Patent Kokoku Publication No. 7691/1969),
(5) Ozonolysis process using a perfluoroalkylolefine as a feedstock (see for example, Japanese Patent Kokai Publication No. 64051/1974), and
(6) Oxidative decomposition process using a ruthenium catalyst and perfluoroolefin in a fluorocarbon solvent (see Journal of Fluorine Chemistry, 13 (1979), pages 175–177).

However, the above exemplified processes have the following disadvantages: for example, a low reaction yield; necessity of severe conditions such as a low reaction temperature from −70° C. to −40° C. or a high reaction temperature from 150° C. to 200° C.; and necessity of use of a corrosive or hazardous reagent or involving difficulties in after-treatment or recovery due to using a metal compound, so that they can not be always effective processes. In particular, the above process (6) has a disadvantage that reaction rate remarkably decreases when water phase exists in the reaction system, so that such a process are not practically applicable for a system containing water phase.

SUMMARY OF THE INVENTION

Therefore, an objective of the present invention is to provide a new process of preparing a perfluoroalkylcarboxylic acid by which at least one of the above-mentioned disadvantage is overcome.

The present invention provides a process of preparing a perfluoroalkylcarboxylic acid by an oxidative decomposition reaction of a perfluoroalkylethylene corresponding to a general formula:

Rf—CH=CH$_2$ wherein Rf is a perfluoroalkyl group containing 2 to 14 carbon atoms (i.e. a C$_{2-14}$ perfluoroalkyl group), so as to obtain a perfluoroalkylcarboxylic acid corresponding to a general formula:

Rf—COOH wherein Rf is the same as the above, characterized in that the reaction is carried out in the presence of an organic solvent which is compatible with and substantially inert to the above reaction, a ruthenium compound as a catalyst and an aqueous solution of at least one of hypochlorous acid or a salt thereof.

DETAILED DESCRIPTION OF THE INVENTION

In the present invention, the perfluoroalkylethylene corresponding to the general formula:

Rf—CH=CH$_2$ wherein Rf is a C$_{2-14}$ perfluoroalkyl group, is used as a feedstock of the reaction.

Such a perfluoroalkylethylene, for example perfluorooctylethylene (C$_8$F$_{17}$—CH=CH$_2$), is stoichiometrically produced by contacting a compound containing a corresponding perfluoroalkyl group, for example, a compound wherein the perfluoroalkyl group bonds to a halogenated ethyl group such as an ethyliodide group (Rf—CH$_2$CH$_2$I such as C$_8$F$_{17}$—CH$_2$CH$_2$I) with sodium hydroxide or potassium hydroxide while methanol or ethanol is refluxed in the system. Such a production process is described in, for example, Journal of Chemical Society, (1950) page 3041 and Journal of Organic Chemistry, 23, (1958) page 1166, the disclosures of which are incorporated by reference into the present specification.

As the perfluoroalkylcarboxylic acid (Rf—COOH) which is produced by the present process, a perfluoroalkylcarboxylic acid having a perfluoroalkyl group having from 2 to 14 carbon atoms is commercially useful, in particular, that having a perfluoroalkyl group having from 6 to 12 carbon atoms, for example, from 6 to 10 is more useful. A particularly useful perfluoroalkylcarboxylic acid is one containing a perfluoroalkyl group which has 7 or 8 carbon atoms. The perfluoroalkyl group may include a straight chain or a branched chain.

In the present process, the perfluoroalkyl group (Rf group) of the perfluoroalkylethylene (Rf—CH=CH$_2$), which is the feedstock for the present process, scarcely decomposes during the reaction and is substantially maintained in the perfluoroalkylcarboxylic acid (Rf—COOH) that is the objective product of the present invention. Accordingly, a perfluoroalkylethylene having a perfluoroalkyl group that corresponds to the perfluoroalkyl group of the perfluorocarboxylic acid as the objective reaction product is used as a feedstock for the present process.

The ruthenium compound which is used as the catalyst in the present process includes, for example, ruthenium metal, ruthenium sesquioxide, ruthenium dioxide, ruthenium tetraoxide, ruthenium hydroxide, ruthenium chloride, ruthenium bromide, ruthenium iodide, and ruthenium sulphate and a hydrate thereof. The ruthenium compound may be used solely or in a mixture with one or more of those ruthenium compounds.

While not wishing to restrict the present process, it is supposed that the following reactions would mainly proceed in the present process.

When any of the above ruthenium compounds other that ruthenium tetraoxide is used, it is converted into a ruthenium tetraoxide form by hypochlorous acid or a salt thereof that is used as a co-oxidant. Accordingly, the catalyst existing in the ruthenium tetraoxide form in the present reaction system oxidatively cleaves the double bond of the perfluoroethylene (Rf—CH=CH$_2$) by its oxidizing performance, and then the perfluorocarboxylic acid having the corresponding perfluoroalkyl group and formic acid are produced as indicated in the following reaction formula (I):

Rf—CH=CH$_2$+2RuO$_4$→Rf—COOH+HCOOH+2RuO$_2$  (I)

The catalyst existing in the ruthenium tetraoxide form further decomposes the formic acid obtained from the above reaction formula (I) to carbon dioxide (CO$_2$) and water (H$_2$O) as indicated in the following reaction formula (II):

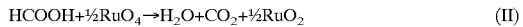

HCOOH+½RuO$_4$→H$_2$O+CO$_2$+½RuO$_2$  (II)

In general, these ruthenium compounds are preferably used in a range from 0.01 to 2 moles per 100 moles of the perfluoroalkylethylene (Rf—CH=CH$_2$) used as the feedstock. In one case in which the amount of the ruthenium compound is less than the lower limit of the above range, the reaction rate may excessively decrease. In the other case in which the amount of the ruthenium compound exceeds the upper limit of the above range, the expensive ruthenium compound is used in a large amount. Therefore, neither of the above cases are preferable from a commercial viewpoint in many cases.

It is not supposed that hypochlorous acid or salt thereof used in the present process substantially directly contributes to the oxidation reaction indicated in reaction formula (I), however, it has a function for being so called co-oxidant, for example, a function to produce or regenerate the ruthenium tetraoxide which functions as a catalyst in the main oxidation reaction indicated in the above formula (I). Therefore, the other compound, which has a function to produce or regenerate the ruthenium tetraoxide from the other ruthenium compounds used as the catalyst, for example peracetic acid, periodic acid or bromic acid or a salt thereof may be used instead of hypochlorous acid or a salt thereof or aqueous solution thereof in the present invention. However, an aqueous solution of hypochlorous acid or a salt thereof which is, in general, easily obtainable in an aqueous solution form, for example an aqueous sodium hypochlorite solution is preferably used.

In the present invention, it is supposed that, when the ruthenium compound charged into the reaction system is other than ruthenium tetraoxide as described above, hypochlorous acid or the salt thereof which functions as a co-oxidant has a function that it converts the ruthenium compound into ruthenium tetraoxide form in the reaction system, and in addition, it re-oxidizes ruthenium dioxide having a lower oxidation number which is resulted from the oxidative leavage reaction of the double bond of the perfluoroalkylethylene so as to generate ruthenium tetraoxide as indicated in the following reaction formula (III):

5/2RuO$_2$+5NaClO→5/2RuO$_4$+5NaCl  (III)

Therefore, the present process may be summarized as the following reaction formula (IV) by combining the formulae (I) to (III):

Rf—CH=CH$_2$+5NaClO→Rf—COOH+H$_2$O+CO$_2$+5NaCl  (IV)

Although the ruthenium compound used in the present process does not appear in the formula (IV), it may be called as a catalyst in a sense in the present process since it proceeds the reaction corresponding to the reaction formula (IV) by existing in the reaction system in a catalytic amount.

In the present process, the concentration of hypochlorous acid or the salt thereof in the aqueous solution is not so critical, but the total amount of hypochlorous acid or the salt thereof added into the reaction system is important. Therefore, the present process may use the aqueous solution which contains hypochlorous acid or the salt thereof at any concentration, but usually a concentration ranging from 5 to 20% by weight, and more preferably from 10 to 15% by weight of an effective amount of chlorine in the aqueous solution is used. The total amount of hypochlorous acid or the salt thereof, particularly sodium hypochlorite to be used is at least 5 moles, preferably up to 6 moles, more preferably up to 5.2 moles per 1 mole of the perfluoroalkylethylene used as the feedstock.

Since the reaction of the present process is exothermic, the aqueous solution of hypochlorous acid or the salt thereof may generally be added to the reaction system in any known manner in which the solution is divided into plural portions each having proper small amount and successively added portion by portion, or added continuously using a dropping funnel or a pumping system.

As the organic solvent which is used in the present invention, a solvent which is compatible with the catalyst and the aqueous phase including the co-oxidant and which is substantially inert in the reaction used in the present process, and accordingly which is substantially neither oxidized nor decomposed during the reaction is selected. In the present invention, the solvent which is compatible with water is intended to mean any of the following cases: a case wherein the solvent dissolves at least a portion of existing water; a case wherein water dissolves at least a portion of the existing solvent; and a case wherein both water and the solvent dissolve existing water and solvent, respectively (in the above three cases, heterogeneous liquid phases are obtained) as well as a case wherein the organic solvent and water dissolve each other (accordingly a homogeneous liquid phase is obtained). In other word, it means that a case wherein the organic solvent and water does not dissolve each other at all is precluded.

As such organic solvents, alcohols, for example tertiary butyl alcohol, nitrites, for example acetonitrile, and ethers, for example ethylene glycol dimethyl ether and 1,3-dioxane may be exemplified. They may be used solely or in a mixture system. The solvent is used in an amount ranging from 0.1 to 20 parts by weight, preferably from 0.2 to 10 parts by weight, and more preferably from 0.5 to 5 parts by weight based on 1 parts by weight of a perfluoroalkylethylene used as the feedstock.

When hypochlorous acid or the salt thereof is used in the present process, they are typically charged in an aqueous solution form so that water generally exists in the reaction system. In such case, the pH value of the reaction system is adjusted in the range from 5 to 10, and preferably from 6 to 8. In particular, when sodium hypochlorite is used as the co-oxidant, sodium hypochlorite may decompose if the pH value is below the lower limit of the above range, and chlorine gas, which is hazardous, is formed together with the increase of consumption amount of sodium hypochlorite. When the pH value is above the upper limit of the above range, the reaction rate may decrease. Accordingly, neither of the above both cases are preferred for proceeding with the reaction.

Accordingly, it is preferred to adjust the pH value of the reaction system by adding a basic substance, which does not inhibit the reaction represented by the formula (IV), as a so-called pH-regulator in an aqueous solution form in order that the pH value of the reaction system is kept within the above range. As such a basic substance, various compounds, for example sodium hydroxide or potassium hydroxide may be used. Sodium hydroxide is preferred since it is advantageous as to its low-cost merit and its easy availability. The basic substance may be added to the reaction system in any known manner in which the solution is divided into a plural portion by portion, or added continuously using a dropping funnel or a pumping system.

The total amount of the basic substance, for example sodium hydroxide, to be added until the reaction terminates amounts to 1.8 to 2.2 moles, and generally about 2 moles based on 1 mole of perfluoroalkylethylene used as the feedstock.

The reaction according to the present process proceeds in a homogeneous liquid phase system consisting of an organic liquid phase and an aqueous phase (accordingly a system in which the mutual solubility between the two phases) is infinite or in a heterogeneous liquid phase system consisting of an organic liquid phase and an aqueous phase (accordingly a system in which the mutual solubility is limited). In addition, the present reaction system may be a mixture system of a solid phase and a liquid phase which includes an undissolved solid phase when the liquid phase does not completely dissolve the catalyst.

The reaction temperature applicable to the present process is preferably in the range from 10 to 50° C., and ore preferably from 20 to 40° C. For example, in producing perfluorooctylcarboxylic acid, it is preferred to apply a reaction temperature in the range from 20 to 40° C. When the reaction temperature is below the lower limit of the above range, the reaction rate may tend to decrease. When the reaction temperature is above the upper limit of the above range, the co-oxidant may tend to decompose. Accordingly, both cases are disadvantageous to the present process.

Since the reaction of the present process is exothermic, it is generally preferred to use a reactor which can maintain the reaction temperature by cooling. As such a reactor, for example, a reactor through which a coolant may be passed interiorly or exteriorly may be used. The reaction may be carried out in either a continuous operation or a batch operation. An increase of the reaction temperature may be avoided by controlling an addition rate of the co-oxidant. The pressure to be applied to the reaction is not particularly restricted, however it may be atmospheric pressure. The reaction time is generally from 1 to 20 hours, preferably from 2 to 15 hours, and particularly from 2 to 10 hours.

On completion of the reaction, a substance which can reduce sodium hypochlorite and ruthenium tetrahydrate (therefore which may be readily oxidized by sodium hypochlorite and ruthenium tetrahydrate) is added to the reaction solution as a reaction terminator in a small amount. This procedure is intended to consume (or decompose), that is reduce, the sodium hypochlorite excessively existing in the reaction system, by which the oxidation property of the ruthenium compound as the catalyst is lost in order to avoid the regeneration or production of ruthenium tetrahydrate in the reaction system, and then, ruthenium tetrahydrate is converted to ruthenium dioxide in a black solid form, which precipitates. As such a terminator of the reaction, for example, methanol, isopropyl alcohol, ethylene or hydrazine may be used.

The precipitated ruthenium dioxide in the black solid form may be isolated or recovered by any known measure, for example, filtration or centrifuging and, if desired, it may be reused afterward. The objective product of the present invention perfluoroalkylcarboxylic acid generally exists in a salt form in the solution after the reaction is completed depending on hypochlorite or the pH-regulator used. For example, when sodium hydroxide is used as the pH-regulator, the carboxylic acid exists in a sodium salt form (—COONa), which may be easily converted to acid form (—COOH) by the addition of a strong acid such as sulfuric acid.

In order to isolate the perfluoroalkylcarboxylic acid, which is the objective product of the present invention, from the reaction system and then refine it, any procedure that is generally known for example, extraction, distillation, recrystallization or column chromatography technique.

EFFECT OF THE INVENTION

Since the present invention may be carried out at very moderate conditions around atmospheric pressure and ordinary temperature, the procedure of the present process may be carried out with ease at a low cost than the conventional processes with respect to facilities, operations and energies requisite to the process.

Furthermore, according to the present invention, as obviously seen from the following Examples, the conversion of the feedstock is higher than that of the conventional processes, and the yield of perfluoroalkylcarboxylic acid, the objective product, may be further improved than the conventional processes.

In the present process, since recovery operation and handling of the catalyst to be used is easier than those of conventional processes, facilities or operations necessary for the present process may be simplified without.

EXAMPLES

In the following examples, the present invention will be illustrated by the Examples with reference to the production of perfluorooctylcarboxylic acid ($C_8F_{17}COOH$), that is a carboxylic acid having 8 carbon atoms in its Rf-group as the objective perfluoroalkylcarboxylic acid. However, the present invention is not limited to such an embodiment, but is also applicable to the production of various carboxylic acids containing a perfluoroalkyl group having various numbers of carbon atoms.

Example 1

In a four-necked flask (500 ml) equipped with a stirrer, a thermometer and two dropping funnels, 40 g (about 0.09 mol) of perfluorooctylethylene ($C_8F_{17}CH=CH_2$), 50 ml of tertiary butyl alcohol, and 0.1 g (0.43% by mol based on $C_8F_{17}CH=CH_2$) of ruthenium dioxide heptahydrate are charged and stirred vigorously maintaining the temperature at 30° C. in a water bath at atmospheric pressure. From one dropping funnel, 213 ml (5 equivalents of NaClO based on $C_8F_{17}CH=CH_2$) of an aqueous sodium hypochlorite solution (concentration: 2.1 mol/liter) is dropped at a rate 5 ml/min. From another dropping funnel, 179 ml (5 equivalents of NaOH based on $C_8F_{17}CH=CH_2$) of an aqueous sodium hydroxide solution (concentration: 1 mol/liter) is dropped in a small amount intermittently while monitoring the pH-value of the reaction solution so as to keep it within a range from 5 to 10.

After dropping of sodium hypochlorite and sodium hydroxide solutions is completed, stirring is continued further two hours while maintaining the temperature at 30° C. before the reaction is completed. After the reaction is completed, 0.5 ml of isopropyl alcohol is added to consume the excess sodium hypochlorite and the existing ruthenium tetraoxide, by which the catalyst is precipitated as a black solid ruthenium dioxide. The precipitated ruthenium dioxide is filtered through a pressure filter equipped with PTFE filter paper having a pore size of 0.5 μm and then 424 g of filtrate is obtained. The filtrate is analyzed using a $^{19}$F-NMR analysis in which trifluoroacetic acid is used as an internal standard substance and is found to contain 40.8 g of perfluorooctylcarboxylic acid ($C_8F_{17}COOH$) that is the objective product (yield: 98%).

Since the objective perfluorooctylcarboxylic acid exists in the form of sodium salt in the filtrate, the perfluorooctylcarboxylic acid may be separated by condensing the liquor, for example, by evaporating the solvent and optionally water with evaporator, and adding an acid such as sulfuric acid so as to precipitate the perfluorooctylcarboxylic acid. The precipitate of and the objective perfluorooctylcarboxylic acid may be filtered to recover the perfluorooctylcarboxylic acid.

Example 2

The procedure of Example 1 is repeated except that one dropping funnel is used, 213 ml (5 equivalents of NaClO based on $C_8F_{17}CH=CH_2$) of an aqueous sodium hypochlorite solution (concentration: 2.1 mol/liter) as well as 29.9 g (2 equivalents of NaOH based on the weight of $C_8F_{17}CH=CH_2$) of an aqueous sodium hydroxide solution (concentration: 24% by weight) are charged into the dropping funnel together, and then the aqueous solution is dropped at a rate of 5 ml/min monitoring the pH-value of the solution within the specified range. Then, a filtrate is obtained which is separated into two layers (the upper layer: 201 g, the lower layer: 137 g). The upper layer of the filtrate is an aqueous phase and the lower layer is a tertiary butyl alcohol phase. As a result of the analysis as in Example 1, 0.2 g of the objective perfluorooctylcarboxylic acid is included in the upper layer (yield: 0.5%), and 41.4 g of the same carboxylic acid is included in the lower layer (yield: 99.5%).

Example 3

The procedure of Example 1 is repeated except that 20 g of perfluorooctylethylene ($C_8F_{17}CH=CH_2$), 244 ml of tertiary butyl alcohol, 107 ml (5 equivalents of NaClO based on $C_8F_{17}CH=CH_2$) of an aqueous sodium hypochlorite solution (concentration: 2.1 mol/liter) as well as 90 ml (2 equivalents of NaOH based on $C_8F_{17}CH=CH_2$) of an aqueous sodium hydroxide solution (concentration: 1 mol/liter) are used. Then, a filtrate is obtained which is separated into two layers (the upper layer: 301 g, lower layer: 133 g). As a result of the analysis as in Example 1, 20.2 g of the objective perfluorooctylcarboxylic acid ($C_8F_{17}COOH$) is included in the upper layer (tertiary butyl alcohol phase) (yield: 97%), and the lower layer (aqueous layer) does not include the perfluorooctylcarboxylic acid.

Example 4

In a flask as used in Example 1, 20 g of perfluorooctylethylene ($C_8F_{17}CH=CH_2$), 300 ml of acetonitrile, and 0.1 g (0.86% by mol based on $C_8F_{17}CH=CH_2$) of ruthenium dioxide heptahydrate are charged and stirred vigorously maintaining the temperature at 30° C. in a water bath at an atmospheric pressure. From one dropping funnel, 107 ml (5 equivalents of NaClO based on $C_8F_{17}CH=CH_2$) of an aqueous sodium hypochlorite solution (concentration: 2.1 mol/liter) is dropped at a rate 0.6 ml/min, and from another dropping funnel, 90 ml (2 equivalents of NaOH based on $C_8F_{17}CH=CH_2$) of an aqueous sodium hydroxide solution (concentration: 1 mol/liter) is dropped continually at a rate 0.4 ml/min ensuring the pH-value of the system to be kept within the pH-value range from 5 to 10. The resulted solution is treated as in Example 1 after dropping is completed, and then the filtrate is obtained which is separated into two layers (the upper layer: 269 g, the lower layer: 175 g). As a result of the analysis as in Example 1, 19.8 g of the objective perfluorooctylcarboxylic acid ($C_8F_{17}COOH$) is included in the upper layer (acetonitrile phase) (yield: 95%), and 0.1 g of the perfluorooctylcarboxylic acid ($C_8F_{17}COOH$) is included in the lower layer (aqueous phase) (yield: 0.5%). The upper layer included 0.2 g of unreacted perfluorooctylethylene.

Comparative Example 1

As a Comparative Example, the procedure of Example 1 is repeated as to the feedstocks, catalysts and reactors except that 1,1,2-trichlorotrifluoroethane is used instead of tertiary butyl alcohol as the solvent. The reaction is started as in Example 1 while dropping 10 ml of aqueous sodium hypochlorite solution and 5 ml of aqueous sodium hydroxide solution, and then stirring is continued for 4 hours after the dropping is finished. However, little of the sodium hypochlorite in the water phase was consumed. And then, 3 g of 20% by weight aqueous hydrazine solution is added to consume the excess sodium hypochlorite and precipitate ruthenium dioxide as a black solid.

The precipitated ruthenium dioxide is filtered through a pressure filter equipped with PTFE filter paper having a pore size of 0.5 μm as well as the water used to wash the flask is similarly filtered to obtain a filtrate which is separated into two layers. The lower layer is analyzed by gas chromatography technique and a 0.5% conversion of perfluorooctylethylene is found, which means that the reaction hardly proceeded.

Comparative Example 2

The procedure of Example 1 is repeated except that 1,1,2-trichlorotrifluoroethane is used instead of tertiary butyl alcohol as the solvent. In this example, sodium hypochlorite is substantially not consumed, but the whole amount of the weighed sodium hypochlorite is added. The pH value of the reaction system is maintained within the range from 8 to 10 only by adding first 5 ml of aqueous sodium hydroxide solution. After the reaction proceeded for 10 hours, 20% by weight aqueous hydrazine solution is added portion by portion gradually in order to consume the excess sodium hypochlorite, and 36 g of the aqueous hydrazine solution was required in such a treatment.

The precipitated ruthenium dioxide is filtered through a pressure filter equipped with PTFE filter paper having a pore size of 0.5 μm and a filtrate which is separated into two layers is obtained. As a result of analysis of the lower layer (1,1,2-trichlorotrifluoroethane phase) as applied in Comparative Example 1, the conversion of perfluorooctylethylene ($C_8F_{17}$—$CH=CH_2$) is not more that 0.5%, which means that the reaction hardly proceeded.

The present disclosure relates to subject matter contained in Japanese Patent Application No. 24874/1997 filed on Feb. 7, 1997 and Japanese Patent Application No. 325897/1997 filed on Nov. 27, 1997, both of which are expressly incorporated herein by reference in their entirety.

What is claimed is:

1. A process of preparing a perfluoroalkylcarboxylic acid by an oxidative decomposition reaction of a perfluoroalkylethylene corresponding to a general formula:

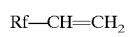

wherein Rf is a perfluoroalkyl group containing 2 to 14 carbon atoms, to obtain a perfluoroalkylcarboxylic acid corresponding to a general formula:

Rf—COOH wherein Rf is the same as the above, and wherein the reaction is carried out in the presence of an organic solvent which is compatible with water and substantially inert to the reaction, a ruthenium compound as a catalyst, and an aqueous solution of at least one of hypochlorous acid or a salt thereof.

2. The process as claimed in claim 1, wherein the organic solvent is at least one selected from the group consisting of tertiary butyl alcohol, acetonitrile, ethylene glycol dimethyl ether and 1,3-dioxane.

3. The process as claimed in claim 1, wherein a pH-value of the reaction is maintained within the range from 5 to 10.

4. The process as claimed in claim 2, wherein a pH-value of the reaction is maintained within the range from 5 to 10.

5. The process as claimed in claim 1, wherein the perfluoroalkyl group is selected from the group consisting of perfluorohexyl group, perfluoroheptyl group, perfluorooctyl group, perfluorononyl group, perfluorodecyl group, perfluoroundecyl group and perfluorododecyl group.

6. The process as claimed in claim 2, wherein the perfluoroalkyl group is selected from the group consisting of perfluorohexyl group, perfluoroheptyl group, perfluorooctyl group, perfluorononyl group, perfluorodecyl group, perfluoroundecyl group and perfluorododecyl group.

7. The process as claimed in claim 3, wherein the perfluoroalkyl group is selected from the group consisting of perfluorohexyl group, perfluoroheptyl group, perfluorooctyl group, perfluorononyl group, perfluorodecyl group, perfluoroundecyl group and perfluorododecyl group.

8. The process as claimed in claim 4, wherein the perfluoroalkyl group is selected from the group consisting of perflourohexeyl group, perfluoroheptyl group, perfluorooctyl group, perfluorononyl group, perfluorodecyl group, perfluoroundecyl group and perfluorododecyl group.

9. The process as claimed in claim 1, wherein the ruthenium compound is selected from the group consisting of ruthenium metal, ruthenium sesquioxide, ruthenium dioxide, ruthenium tetraoxide, ruthenium hydroxide, ruthenium chloride, ruthenium bromide, ruthenium iodide, ruthenium sulphate and a hydrate thereof.

10. The process as claimed in claim 2, wherein the ruthenium compound is selected from the group consisting of ruthenium metal, ruthenium sesquioxide, ruthenium dioxide, ruthenium tetraoxide, ruthenium hydroxide, ruthenium chloride, ruthenium bromide, ruthenium iodide, ruthenium sulphate and a hydrate thereof.

11. The process as claimed in claim 3, wherein the ruthenium compound is selected from the group consisting of ruthenium metal, ruthenium sesquioxide, ruthenium dioxide, ruthenium tetraoxide, ruthenium hydroxide, ruthenium chloride, ruthenium bromide, ruthenium iodide, ruthenium sulphate and a hydrate thereof.

12. The process as claimed in claim 4, wherein the ruthenium compound is selected from the group consisting of ruthenium metal, ruthenium sesquioxide, ruthenium dioxide, ruthenium tetraoxide, ruthenium hydroxide, ruthenium chloride, ruthenium bromide, ruthenium iodide, ruthenium sulphate and a hydrate thereof.

13. The process as claimed in claim 5, wherein the ruthenium compound is selected from the group consisting of ruthenium metal, ruthenium sesquioxide, ruthenium dioxide, ruthenium tetraoxide, ruthenium hydroxide, ruthenium chloride, ruthenium bromide, ruthenium iodide, ruthenium sulphate and a hydrate thereof.

14. The process as claimed in claim 6, wherein the ruthenium compound is selected from the group consisting of ruthenium metal, ruthenium sesquioxide, ruthenium dioxide, ruthenium tetraoxide, ruthenium hydroxide, ruthenium chloride, ruthenium bromide, ruthenium iodide, ruthenium sulphate and a hydrate thereof.

15. The process as claimed in claim 7, wherein the ruthenium compound is selected from the group consisting of ruthenium metal, ruthenium sesquioxide, ruthenium dioxide, ruthenium tetraoxide, ruthenium hydroxide, ruthenium chloride, ruthenium bromide, ruthenium iodide, ruthenium sulphate and a hydrate thereof.

16. The process as claimed in claim 8, wherein the ruthenium compound is selected from the group consisting of ruthenium metal, ruthenium sesquioxide, ruthenium dioxide, ruthenium tetraoxide, ruthenium hydroxide, ruthenium chloride, ruthenium bromide, ruthenium iodide, ruthenium sulphate and a hydrate thereof.

17. The process of claim 1, wherein said Rf is a perfluoroalkyl group having 6 to 12 carbon atoms.

18. The process of claim 1, wherein said Rf is a perfluoroalkyl group having 6 to 10 carbon atoms.

19. The process of claim 1, wherein said organic solvent is present in an amount ranging from 0.1 to 20.0 parts by weight based on 1 part by weight of the perfluoroalkylethylene.

20. The process of claim 1, wherein said hypochlorous acid or salt thereof is present in an amount ranging from 5 to 20% by weight of an effective amount of chlorine in the aqueous solution.

* * * * *